US011511085B2

United States Patent
Boucher et al.

(10) Patent No.: US 11,511,085 B2
(45) Date of Patent: Nov. 29, 2022

(54) TORQUE COIL AND METHOD

(71) Applicant: Heraeus Deutschland GmbH & Co. KG, Hanau (DE)

(72) Inventors: Colin Boucher, St. Paul, MN (US); Ngac Ba Dao, Oakdale, MN (US); Megan T. Brosnan, Plymouth, MN (US); Shawn D. Bluhm, Center City, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 334 days.

(21) Appl. No.: 15/776,833

(22) PCT Filed: Nov. 18, 2015

(86) PCT No.: PCT/US2015/061354
§ 371 (c)(1),
(2) Date: May 17, 2018

(87) PCT Pub. No.: WO2017/086954
PCT Pub. Date: May 26, 2017

(65) Prior Publication Data
US 2018/0339139 A1    Nov. 29, 2018

(51) Int. Cl.
*A61M 25/09* (2006.01)
*A61B 5/00* (2006.01)
(Continued)

(52) U.S. Cl.
CPC ......... *A61M 25/09016* (2013.01); *A61B 5/01* (2013.01); *A61B 5/02154* (2013.01);
(Continued)

(58) Field of Classification Search
CPC ........ A61M 25/09; A61M 2025/09091; A61M 2025/09083; A61M 2025/09058;
(Continued)

(56) References Cited

U.S. PATENT DOCUMENTS 4,979,795 A     12/1990  Mascarenhas
5,060,660 A  *  10/1991  Gambale ........... A61M 25/0144
                                                    600/585

(Continued)

FOREIGN PATENT DOCUMENTS

EP    0661072    7/1995
EP    1379311    1/2004
(Continued)

OTHER PUBLICATIONS

The International Search Report and Written Opinion for International Application No. PCT/US2015/061354 dated Jul. 21, 2016 (13 pgs.).

*Primary Examiner* — Daniel L Cerioni
(74) *Attorney, Agent, or Firm* — Dicke, Billig & Czaja, PLLC

(57) ABSTRACT

A torque coil 10 includes an inner wire layer 14 helically wound in a constricted state. An outer wire layer 18 is helically wound over the inner wire layer in a constricted state. An outer polymer cover 20 surrounds the inner and outer layers thereby securing the inner and outer layers within the outer polymer cover.

17 Claims, 13 Drawing Sheets

(51) Int. Cl.
*A61B 5/01* (2006.01)
*A61B 5/0215* (2006.01)
*F16C 1/02* (2006.01)
A61M 25/01 (2006.01)
A61N 1/05 (2006.01)
A61B 34/20 (2016.01)

(52) U.S. Cl.
CPC ........... *A61B 5/6851* (2013.01); *A61M 25/09* (2013.01); *F16C 1/02* (2013.01); *A61B 2034/2061* (2016.02); *A61M 25/0102* (2013.01); *A61M 2025/09091* (2013.01); *A61N 1/056* (2013.01)

(58) Field of Classification Search
CPC ............ A61M 25/005; A61M 25/0053; A61M 25/0054; A61M 2025/0059; A61M 25/0141; A61M 25/0144; A61M 25/0147; A61M 2025/09066; A61M 2025/09075; A61M 25/09016; A61B 5/6851; A61B 5/01; A61B 5/02154; F16C 1/02
USPC ........................................................ 600/585
See application file for complete search history.

(56) References Cited

U.S. PATENT DOCUMENTS

| | | | | |
|---|---|---|---|---|
| 5,103,543 A | * | 4/1992 | Hodgson | A61M 25/005 29/896.9 |
| 5,147,317 A | * | 9/1992 | Shank | A61M 25/09 600/434 |
| 5,554,139 A | * | 9/1996 | Okajima | A61M 25/005 600/433 |
| 5,932,035 A | | 8/1999 | Koger et al. | |
| 6,139,557 A | * | 10/2000 | Passafaro | A61M 25/09 600/585 |
| 6,589,227 B2 | | 7/2003 | Sonderskov Klint | |
| 6,685,696 B2 | | 2/2004 | Fleischhacker et al. | |
| 7,077,811 B2 | | 7/2006 | Vrba et al. | |
| 7,621,904 B2 | * | 11/2009 | McFerran | A61M 25/0041 604/525 |
| 7,713,215 B2 | * | 5/2010 | Shriver | A61M 25/09 604/95.04 |
| 8,117,817 B2 | | 2/2012 | Markham et al. | |
| 8,157,751 B2 | | 4/2012 | Adams et al. | |
| 8,250,844 B2 | | 8/2012 | Markham | |
| 8,273,100 B2 | | 9/2012 | Martinez | |
| 8,403,867 B2 | | 3/2013 | Nowak, Jr. | |
| 8,480,598 B2 | | 7/2013 | Nelson, III et al. | |
| 8,540,695 B2 | | 9/2013 | Shimogami et al. | |
| 8,647,323 B2 | | 2/2014 | Guo et al. | |
| 8,702,746 B2 | | 4/2014 | Tekulve et al. | |
| 8,798,767 B2 | | 8/2014 | Foster et al. | |
| 8,961,434 B2 | | 2/2015 | Miyata et al. | |
| 9,370,639 B2 | | 6/2016 | Plassman et al. | |
| 2005/0096567 A1 | * | 5/2005 | Reynolds | A61M 25/09 600/585 |
| 2005/0119615 A1 | * | 6/2005 | Noriega | A61M 25/09 604/95.04 |
| 2006/0047224 A1 | * | 3/2006 | Grandfield | A61M 25/09 600/585 |
| 2007/0083132 A1 | | 4/2007 | Sharrow | |
| 2009/0198153 A1 | * | 8/2009 | Shriver | A61M 25/09 600/585 |
| 2009/0299332 A1 | * | 12/2009 | Shireman | A61M 25/09 604/526 |
| 2014/0236120 A1 | * | 8/2014 | Tsai | A61M 25/0136 604/506 |

FOREIGN PATENT DOCUMENTS

| | | |
|---|---|---|
| EP | 1933921 | 6/2008 |
| WO | 2015063781 | 5/2015 |
| WO | 2017087149 | 5/2017 |

* cited by examiner

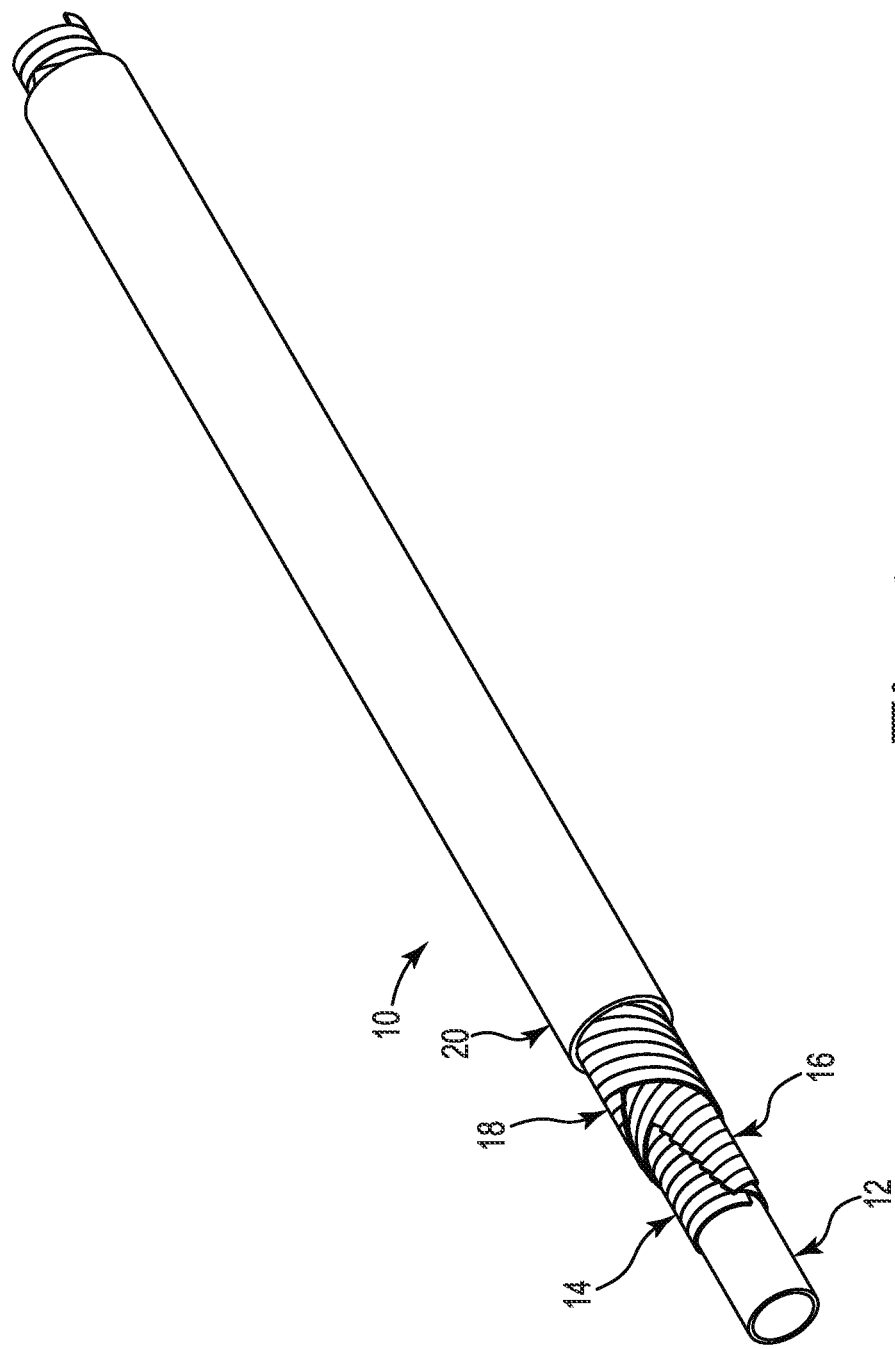

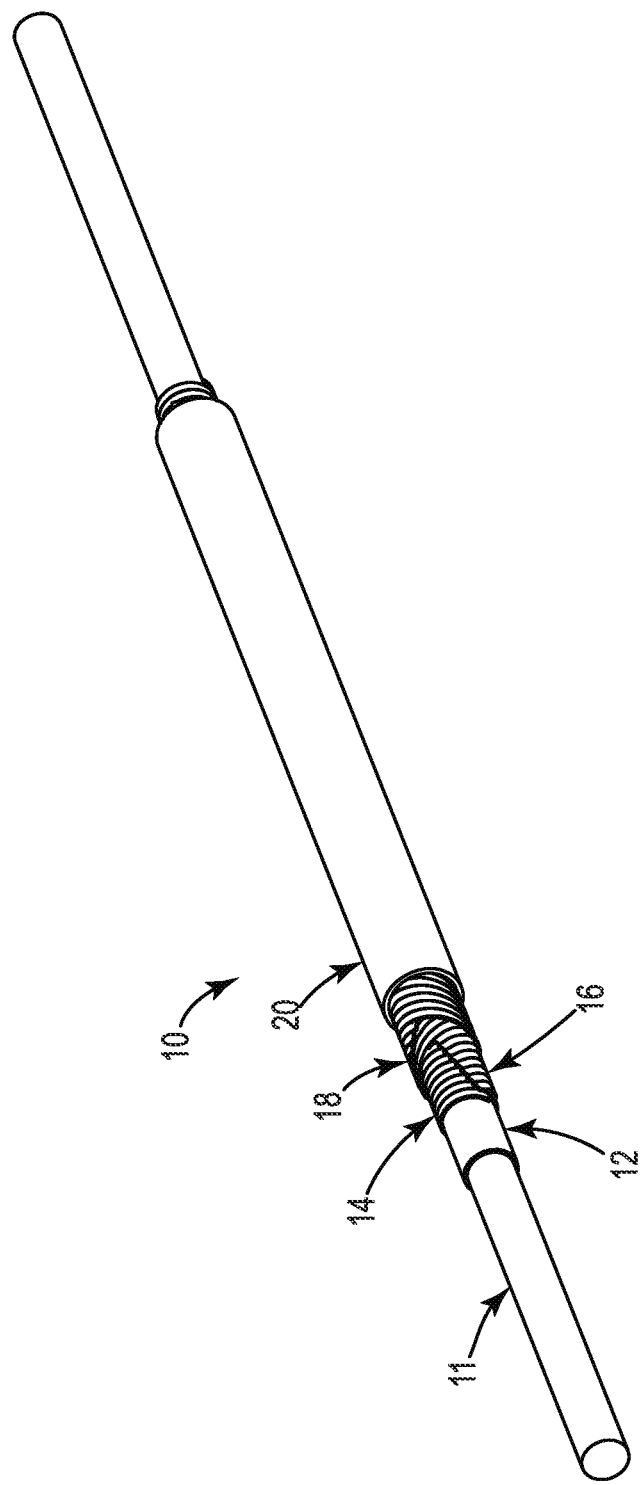

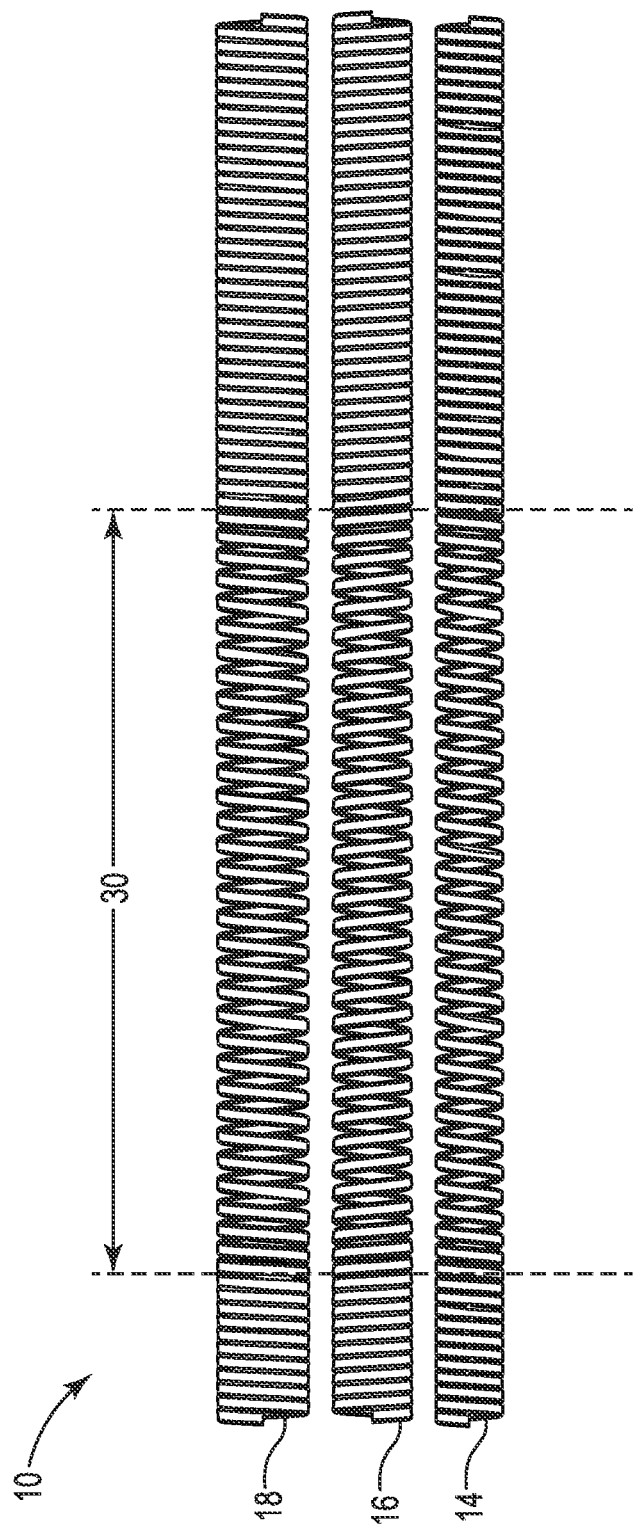

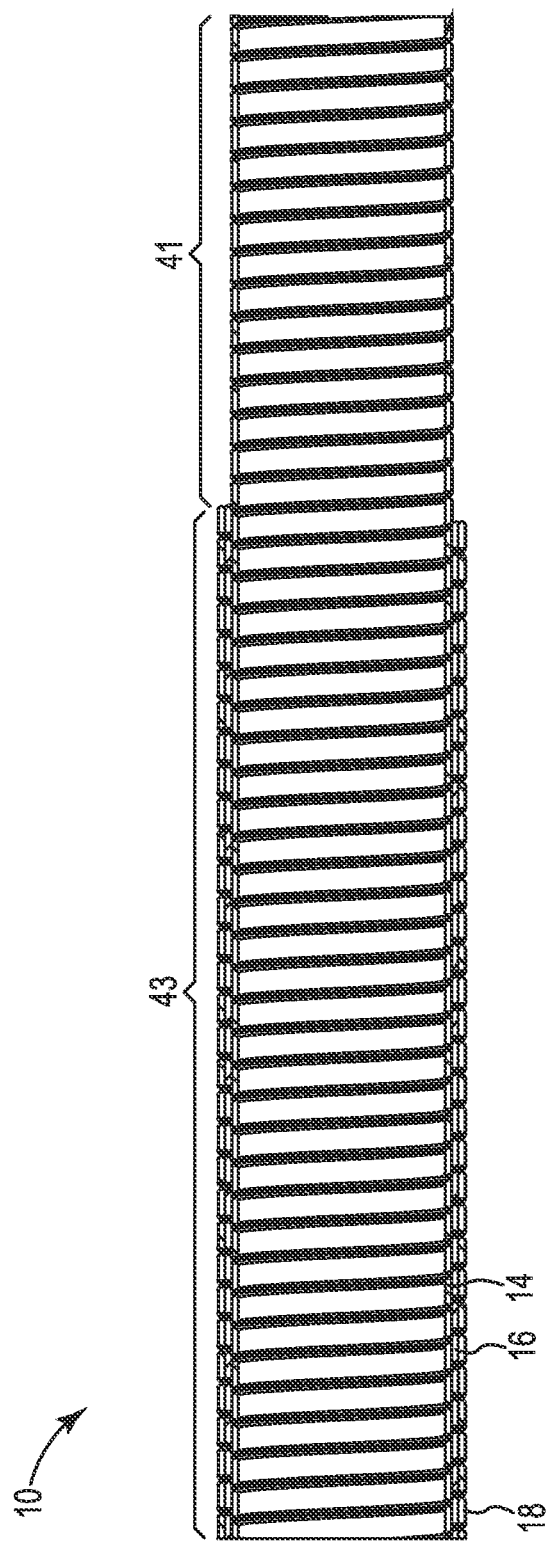

TORQUE COIL AND METHOD

CROSS-REFERENCE TO RELATED APPLICATIONS

This Utility Patent Application claims priority under 35 U.S.C. § 371 to International Application Serial No. PCT/US2015/061354, filed Nov. 18, 2018; which is incorporated herein by reference in its entirety.

BACKGROUND

The present invention relates to helically-wound torque coil and related method. In one embodiment, a coil includes a single wire that is tightly wound over itself to form a multi-layer coil with a hollow lumen. In some instances, however, such coils use solder or brazing to secure ends of the coil to prevent its uncoiling. Because there are limitations to use of such approaches, there is a need for the present invention.

BRIEF DESCRIPTION OF THE DRAWINGS

FIGS. 1a and 1b illustrate partial cut-away perspective views of torque coils in accordance with embodiments.

FIG. 5 illustrates an exploded view of portions of a torque coil in accordance with one embodiment.

FIGS. 6a-6d illustrate perspective and cross-sectional views of torque coils in accordance with embodiments.

DETAILED DESCRIPTION

Figure 2A:
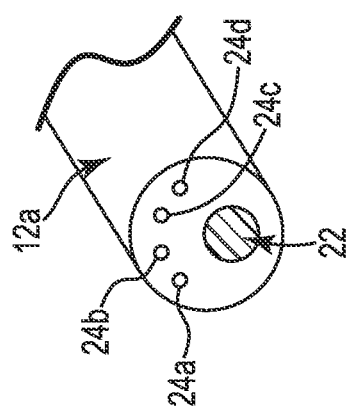
FIGS. 2a-2c illustrate partial perspective views of a torque coil in accordance with embodiments.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

One embodiment includes a torque coil with an inner wire layer helically wound in a constricted state. An outer wire layer is helically wound over the inner wire layer in a constricted state. An outer polymer cover surrounds the inner and outer wire layers thereby securing the wire layers within the outer polymer cover. In one embodiment, the torque coil also includes a core of a polymer material within the inner wire layer, such that the inner and outer wire layers are secured between the core and the outer polymer cover. Securing the inner and outer wire layers in this way allows the torque coil in some embodiments to be readily assembled and provide excellent one-to-one torque with very high flexibility.

In one embodiment, the torque coil includes polymer material from the core or polymer material from the outer polymer cover to penetrate between filars in at least one of the inner and outer wire layers. This provides stiffening of the torque coil in the areas of penetration.

In one embodiment, the torque coil includes an intermediate wire layer helically wound over the inner wire layer in a constricted state, the outer wire layer being helically wound over the intermediate wire layer. Additional intermediate layers provide additional stiffness and add further strength to the torque coil to prevent kinking and provide resistance to elongation, and has excellent compression resistance between adjacent filars.

In one embodiment, the torque coil includes a penetrated section (4) where the polymer material of the outer polymer cover penetrates between adjacent filars in the outer wire layer in a of the torque coil and a non-penetrated section (54) where the polymer material of the outer polymer cover does not significantly penetrate between adjacent filars in the outer wire layer in a of the torque coil. The torque coil accordingly has increased relative flexibility in the non-penetrated section (54) and has decreased relative flexibility in the penetrated section (4), which is useful in many applications, such as within the vasculature of a human or animal.

In one embodiment, the torque coil includes a tight-wound section where at least one of the inner and outer wire layers is tight wound and an open-wound section where at least one of the inner and outer wire layers is open wound. The torque coil accordingly has increased relative flexibility in the open-wound section and has decreased relative flexibility in the tight-wound section, which is useful in many applications, such as within the vasculature of a human or animal.

In one embodiment, the torque coil includes a full-wire layer section where both the inner and outer wire layers are within the full-wire layer section and a partial-wire layer section where the outer wire layer is not within the partial-wire layer section. The torque coil accordingly has increased relative flexibility in the partial-wire layer section and has decreased relative flexibility in the full-wire layer section, which is useful in many applications, such as within the vasculature of a human or animal.

In one embodiment, the torque coil includes a pull wire is attached directly to at least one of the wire layers adjacent a distal end of the torque coil. This is useful in some applications that use a deflectable catheter and avoids the use of a pull ring, thereby saving expense and manufacturing time.

In one embodiment, the outer polymer cover of the torque coil secures the inner and outer layers without use of welding, brazing or soldering. This allows assemble of the toque coil without damaging a polymer core with heat from welding, brazing or soldering.

In one embodiment, the torque coil is configured for high-speed rotation and one-to-one torque, which is useful in many applications, such as within the vasculature of a human or animal.

In one embodiment, the torque coil has a lumen diameter is between 0.008 inches and 0.220 inches, the diameter of the coil is between 0.01 inches and 0.250 inches, and the diameter of the wire is between 0.0005 inches and 0.004 inches. Such dimensions make the torque coil useful in many applications, such as catheter or related application within the vasculature of a human or animal.

In one embodiment, the torque coil includes a polymer core and an inner wire layer helically wound in a constricted state over the polymer core. An outer wire layer is helically wound over the inner wire layer in a constricted state. An outer polymer cover surrounds the inner and outer wire layers thereby securing the wire layers between the polymer core and the outer polymer cover. Securing the inner and outer wire layers in this way allows the torque coil in some embodiments to be readily assembled and provide excellent one-to-one torque with very high flexibility.

In one embodiment, the torque coil has increased relative flexibility in flexible section and has decreased relative flexibility in stiff section, which is useful in many applications, such as within the vasculature of a human or animal.

In one embodiment, the stiff section of the torque coil includes a section in which the polymer material of the outer polymer cover penetrates between adjacent filars in the outer wire layer in a of the torque coil or a section in which at least one of the inner and outer wire layers is tight wound or a section in which both the inner and the outer wire layer is contained within the flexible section.

In one embodiment, the flexible section of the torque coil includes a section in which the polymer material of the outer polymer cover does not significantly penetrate between adjacent filars in the outer wire layer in a of the torque coil, or a section in which at least one of the inner and outer wire layers is open wound, or a section wherein the outer wire layer is not within the flexible section.

One embodiment includes a method of forming a torque coil including forming a polymer core and helically winding an inner wire layer in a constricted state over the polymer core. An outer wire layer is helically wound over the inner wire layer in a constricted state. An outer polymer cover is formed to surround the inner and outer wire layers thereby securing the wire layers between the polymer core and the outer polymer cover. Securing the inner and outer wire layers in this way allows the torque coil in some embodiments to be readily assembled and provide excellent one-to-one torque with very high flexibility.

In one embodiment, the method includes temporarily securing one of the inner and outer wire layers with a clamp until the outer polymer cover secures the inner and outer wire layers between the core and the outer polymer cover. This prevents the wire layers from unwinding and holds the constricted state. Because the wire layers remain constrained, there is no slippage between the wire layers, thereby providing the torque coil with excellent one-to-one torque.

In one embodiment, the method includes forming the outer polymer while controlling the polymer material of the outer polymer cover such that it penetrates between adjacent filars in the outer wire layer of the torque coil in a penetrated section (4) and forming the outer polymer while controlling the polymer material of the outer polymer cover such that it does not significantly penetrate between adjacent filars in the outer wire layer in a of the torque coil in a non-penetrated section (54) such that the torque coil has increased relative flexibility in the non-penetrated section (54) and has decreased relative flexibility in the penetrated section (4), which is useful in many applications, such as within the vasculature of a human or animal.

In one embodiment, the method includes winding the inner or outer wire layer with a tight-wound section in which at least one of the inner and outer wire layers is tight wound and winding the inner or outer wire layer with an open-wound section in which at least one of the inner and outer wire layers is open wound, such that the torque coil has increased relative flexibility in the open-wound section and has decreased relative flexibility in the tight-wound section, which is useful in many applications, such as within the vasculature of a human or animal.

In one embodiment, the method includes winding the inner and outer wire layer with a full-wire layer section in which both the inner and outer wire layers are within the full-wire layer section and winding the inner and outer wire layer with a partial-wire layer section in which the outer wire layer is not within the partial-wire layer section, such that the torque coil has increased relative flexibility in the partial-wire layer section and has decreased relative flexibility in the full-wire layer section, which is useful in many applications, such as within the vasculature of a human or animal.

FIG. 1a illustrates a partial cut-away perspective view of a helically-wound torque coil 10 in accordance with one embodiment. In one embodiment, torque coil 10 includes a core 12, which in one embodiment is a layer of polymer material that is customizable to various applications, as will be further discussed below. In one embodiment, torque coil 10 further includes an inner wire layer 14 helically wound over core 12 and an intermediate wire layer 16 helically wound over inner wire layer 14 (in the figure, a portion of intermediate wire layer 16 is cut away to show inner wire layer 14 below it). Torque coil 10 further includes an outer wire layer 18 helically wound over intermediate wire layer 16 (in the figure, a portion of outer wire layer 18 is cut away to show intermediate wire layer 16 below it). Outer polymer cover 20 is formed over the combination of core 12, inner wire layer 14, intermediate wire layer 16, and outer wire layer 18, thereby securing the combination together.

In one embodiment, inner wire layer 14 is tightly wound in a constricted state over core 12, and each subsequent wire layer, that is, intermediate wire layer 16, outer wire layer 18, etc., is tightly wound in a constricted state over the previous wire layer across the entire layer. In one embodiment, a single wire filar is used for each of inner, intermediate, and outer wire layers 14, 16 and 18 without ever being cut or interrupted. In this way, inner wire layer 14 is wound on core 12, and then intermediate wire layer 16 is wound back over inner wire layer 14 without ever cutting the wire that is used to wind the layers. The same can be done for outer wire layer 18 and for any additional intermediate wire layers.

In one embodiment, a wire is broken or cut between each adjacent wire layer, but because each wire layer is tightly wound in a constricted state, each immediately adjacent over wire layer, that is, the wire layer subsequently wound over the previous wire layer, constrains the previous wire layer and prevents its unwinding. Outer wire layer 18 in the embodiment of FIG. 1a is then constrained by outer polymer cover 20, as is discussed further below. Because all wire layers are constrained, there is no slippage between the wire layers. In this way torque coil 10 has excellent "one-to-one" torque, that is, a single full rotation at one end of torque coil 10 results in a single full rotation at the opposite end, rather than something less than a full rotation. Although the illustrated embodiment in FIG. 1 has three wire layers (14, 16, 18) between core 12 and outer polymer cover 20, using just two wire layers (for example, inner wire layer 14 and outer wire layer 18), or using more than three layers are also possible for torque coil 10 by adding multiple additional intermediate layers.

In the example illustrated in FIG. 1*a*, inner wire layer 14 is illustrated as helically wound with a pitch in a first direction, while intermediate wire layer 16 is helically wound with a pitch in a second direction that is reverse relative to the first direction. Outer wire layer 18 is then illustrated as helically wound with a pitch substantially in the first direction, similar to inner wire layer 14. Reverse winding in this way allows torque coil 10 to be used in rotating applications without collapsing in or winding open with the rotation of torque coil 10. Reverse winding provides additional stability to torque coil 10 for bi-directional rotational applications, such that it can be rotated in both clockwise and counterclockwise directions without collapsing in or winding open with the rotation. Such an embodiment may be useful in various rotational intravascular applications. Furthermore, torque coil 10 is extremely resistant to kinking and resistant to elongation and has excellent compression resistance between adjacent filars, such that it may be useful in intravascular applications requiring pushing, pulling and bending of torque coil 10. Despite these strengths and excellent bi-directional turning, torque coil 10 also has excellent flexibility.

FIG. 1*b* illustrates one embodiment of torque coil 10, including core 12, inner wire layer 14 wound over core 12, intermediate wire layer 16 wound over inner wire layer 14, outer wire layer 18 wound over intermediate wire layer 16 and outer polymer cover 20 formed over outer wire layer 18. In the illustrated embodiment, mandrel 11 is provided within core 12. In some embodiments, core 12 is a polymer layer that is provided over mandrel 11. Wire layers 14, 16 and 18 are then wound over core 12 as described above, each wire layer holding and constraining the prior wire layer. Outer polymer cover 20 is then formed over the prior wire layers. Because outer polymer cover is configured to sufficiently constrain the wire layers below it in some embodiments, once outer polymer cover 20 is in place, mandrel 11 can be removed. In such case, core 12 will have an inner lumen (such as that illustrated and discussed below in FIG. 2*c*) that can be filled or used in various applications as discussed.

Figure 2B:
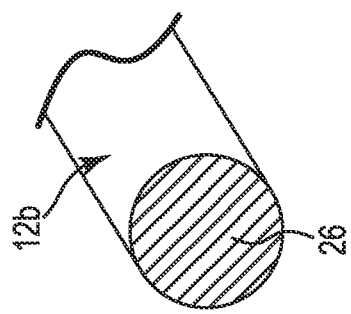
Figure 2C:
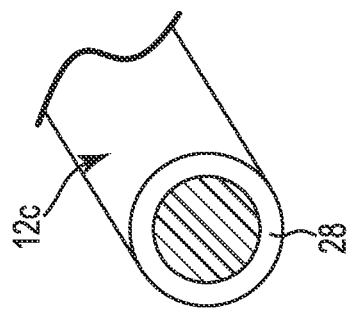

FIGS. 2*a*-2*c* illustrate various embodiments of core 12 of torque coil 10. As illustrated, core 12 is readily adaptable for various applications. In one embodiment, core 12 is a polymer layer that is configured with a plurality of lumens. For example, in one embodiment core 12*a*, illustrated in FIG. 2*a*, includes a main lumen 22. Main lumen 22 can be configured, for example, to receive a guidewire, which is useful for placing torque coil 10 within the vasculature system of a human or animal. Peripheral lumens 24*a*-24*d* are provided in one embodiment adjacent each other and to the main lumen 22 for receiving sensing wires or other wire-like structures, for providing independent passage for fluids, or for other purposes.

Because core 12 is readily formed by extruding, injection molding or the like, one skilled in the art understands that a variety of configurations, shapes and sizes of core 12 are available for torque coil 10. For example, core 12*b* illustrated in FIG. 2*b* is completely solid. Core 12*c*, illustrated in FIG. 2*c*, has a relatively thick perimeter section 28 defining a single lumen through its center. Various other examples and combinations are possible, such as having more lumens that are adjacent or coaxial.

Furthermore, in one embodiment, core 12 is rigid enough that it is capable of functioning as a mandrel and inner wire layer 14 is wound directly on to core 12, with the subsequent wire layers wound over inner wire layer 14. In other embodiments, where core 12 does not have sufficient rigidity to function as a mandrel, inner wire layer 14 can be wound over a more rigid mandrel 11 as discussed above, which can then be subsequently removed once all wire layers are sufficiently constrained, such as by outer polymer cover 20.

In one embodiment, the combination of core 12 and outer polymer cover 20 secure and hold wire layers 14, 16, 18 in place. Prior examples of winding a single wire onto itself to form multiple layers required using braze or solder or rely on welding or fusing the layers in order to secure the layers together and preventing their unwinding. In some embodiments, torque coil 10 cannot use braze, solder, welding or fusing, however, since all of these methods of securing the layers include application of significant heat that can damage core 12 in some instances. For example, when core 12 is a molded polymer component, welding or brazing wire layers 14, 16, 18 to secure them, will also melt core 12 and damage its functionality, for example, by closing off of partially changing diameter of lumens 22, 24*a*, 24*b*, 24*c*, 24*d*.

As such, rather than using braze, solder, welding, fusing or the like, torque coil 10 coats the outer wire layer 18, in the illustrated example, with outer polymer cover 20. Outer polymer cover 20 can be any of a variety of biocompatible polymers that will secure wire layers 14, 16, 18 and prevent their unwinding, even when the wire layers of torque coil 10 are wound in a constricted state.

Figure 3B:
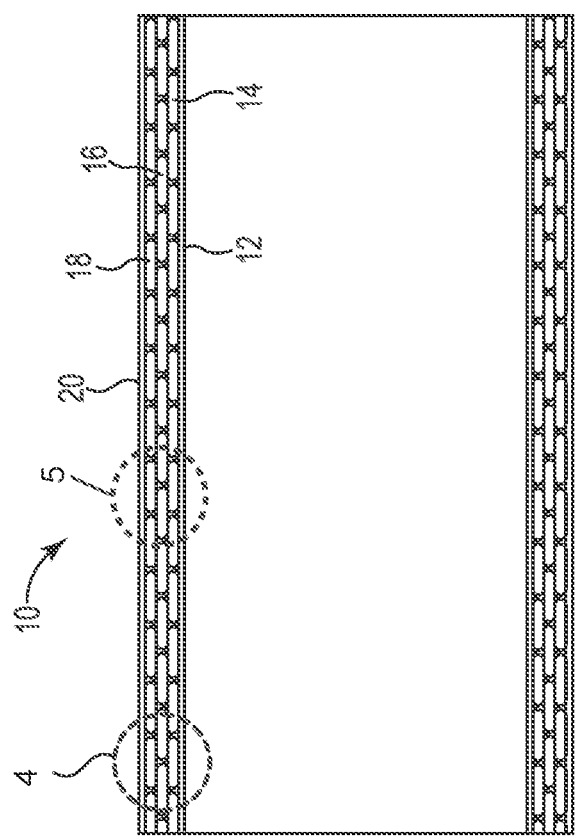
FIG. 3a-3b illustrate perspective and front views of a cross-sectional portion of a torque coil in accordance with one embodiment.
Figure 3A:
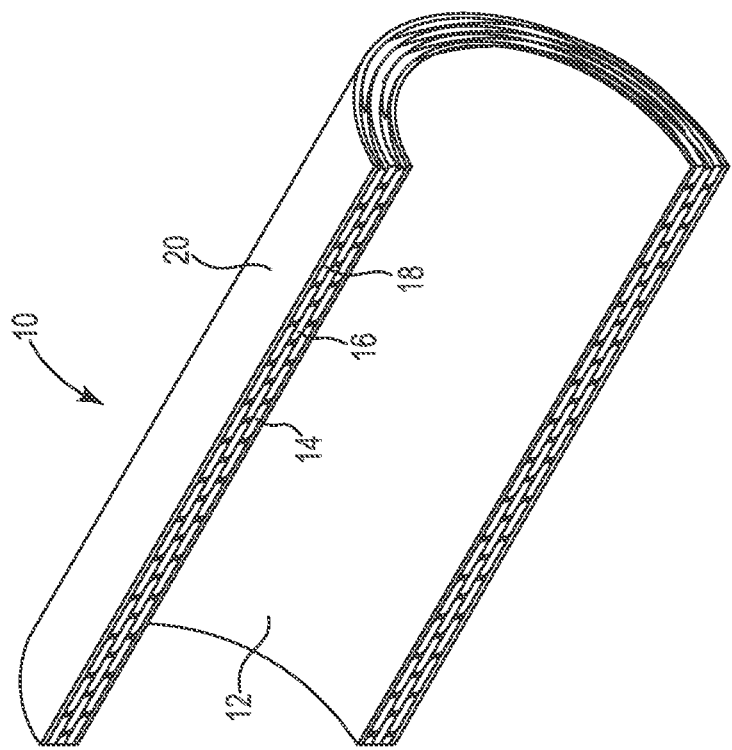

FIGS. 3*a*-3*b* are sectional views illustrating wire layers 14, 16, 18 secured between core 12 and outer polymer cover 20. In one embodiment, a polymer is flowed over wire layers 14, 16 and 18 and then allowed to solidify thereby forming outer polymer cover 20. Once solidified, outer polymer cover 20 has enough rigidity to prevent wire layers 14, 16 and 18 from unwinding.

Figure 4:
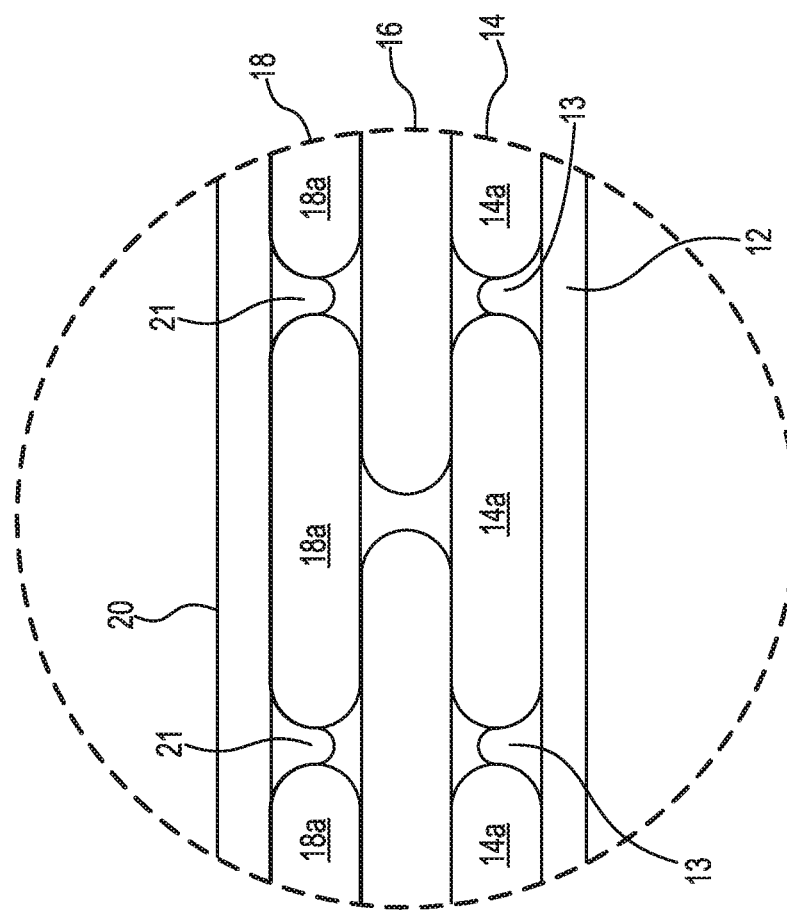
FIG. 4 illustrates an enlarged cross-sectional view of a portion of a torque coil in accordance with one embodiment.

FIG. 4 is an enlarged detailed section 4 shown in dotted lines in FIG. 3*b*. In one embodiment, each of wire layers 14, 16 and 18 are tightly wound over a preceding layer, that is, the wire filar used to wind each wire layer is helically wound such that each filar in a layer is immediately adjacent another filar on either side. In one embodiment, outer wire layer 18 is helically wound with a single wire such that small spaces are left between adjacent filars 18*a* within outer layer 18. As illustrated in FIG. 4, small amounts of material 21 from outer polymer cover 20 flow into these small spaces between adjacent filars 18*a* within outer wire layer 18. In one embodiment, this flow of material 21 can be controlled in order to improve the overall performance of torque coil 10.

In some applications it can be useful for torque coil 10 to have variable stiffness along its length. As such, the melting of a polymer in forming outer polymer cover 20 can be controlled such that more material 21 penetrates into adjacent filars 18*a* within outer wire layer 18 in certain sections of length along torque coil 10, while in other section of length along coil 10 only small amounts or no material 21 penetrates into outer wire layer 18. In this way, some sections (non-penetrated) of torque coil 10 will be more flexible from the wire portions within wire layers 14, 16 and 18, while other sections (penetrated) of torque coil 10 will be stiffer where polymer material 21 is allowed to penetrate and limit motion of torque coil 10 within outer wire layer 18.

In addition, because in some embodiments of torque coil 10 core 12 can also be formed from a polymer material, it too can be controlled such that material 13 from core 12 penetrates in between filars 14*a* of inner layer 14, thereby adding more stiffness to torque coil 10 in those areas, as also illustrated in FIG. 4.

In addition to controlling core 12 and outer polymer cover 20 and penetration of material 21, 13 from these layers into inner and outer wire layers 14 and 18 to vary stiffness of torque coil 10, other embodiments of torque coil 10 allow further adjustments to the flexibility and/or deflectability of torque coil 10. FIG. 5 illustrates a portion of torque coil 10, where wire layers 14, 16, and 18 are exploded apart, and core 12 and outer polymer cover 20 are removed. In the exploded view of the figure, wire layers 14, 16, and 18 are aligned so that open-wound section 30 is illustrated between the dotted lines.

Within open-wound section 30, each of wire layers 14, 16, and 18 are "open wound" such that each filar within each wire layer 14, 16, and 18 is spaced apart from each adjacent filar. As such, when wire layers 14, 16, and 18 are assembled between core 12 and outer polymer cover 20, torque coil 10 is readily deflectable in open-wound section 30. This may be useful in certain applications, such as when torque coil 10 is used within the vascular system of a human or animal and needs to deflect within the tortuous path of the vasculature.

Outside open-wound section 30, torque coil 10 in FIG. 5 is illustrated as "tight wound" such that each filar within each of wire layers 14, 16, and 18 are immediately adjacent each other filar on either side. In these tight-wound sections, torque coil 10 will have significantly less ability to deflect compared to that in open-wound section 30. This variable flexibility along the length of torque coil 10 is useful in some applications. The flexibility of open-wound section 30 can be useful for navigation, whereas the relatively stiffer portions outside open-wound section 30 are useful where high push and/or pull strength is needed. Further stiffening in these tight wound areas may be achieved with penetration of material into the layers as discussed above.

FIGS. 6a-6d illustrate other embodiments of torque coil 10. As illustrated, wire layers 14, 16, and 18 layers each vary in length, thereby also varying the overall flexibility of torque coil 10 along its length. In one embodiment illustrated in FIGS. 6a-6b, inner wire layer 14 is a wire helically wound over a core (not visible in FIGS. 6a-6b) similarly to previously-described embodiments. Intermediate wire layer 16 is then wound over inner wire layer 14, but then terminated such that it covers less than the entire length of torque coil 10. Accordingly, there is a first partial wire layer section 42 of torque coil 10 in which only inner wire layer 14 is wound over core 12. Also, there is a second partial wire layer section 44 of torque coil 10 in which inner wire layer 14 is wound over core 12 and intermediate wire layer 16 is wound over inner wire layer 14. Finally, outer wire layer 18 is wound over intermediate wire layer 16 in an even shorter section of torque coil 10. Accordingly, there is a full-wire layer section 46 of torque coil 10 in which inner wire layer 14 is wound over core 12, intermediate wire layer 16 is wound over inner wire layer 14, and outer wire layer 18 is would over intermediate wire layer 16.

Figure 6A:
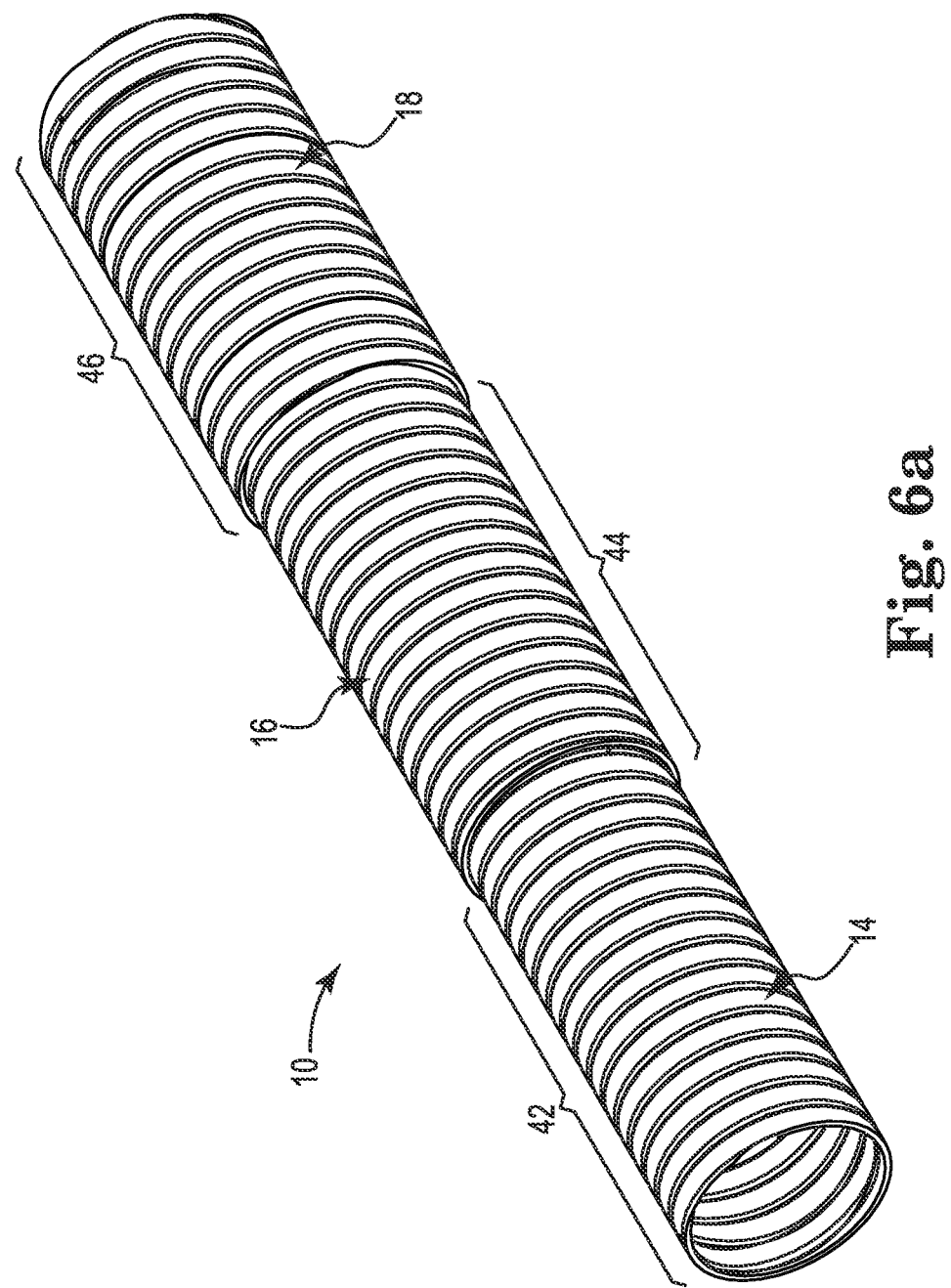
Figure 6B:
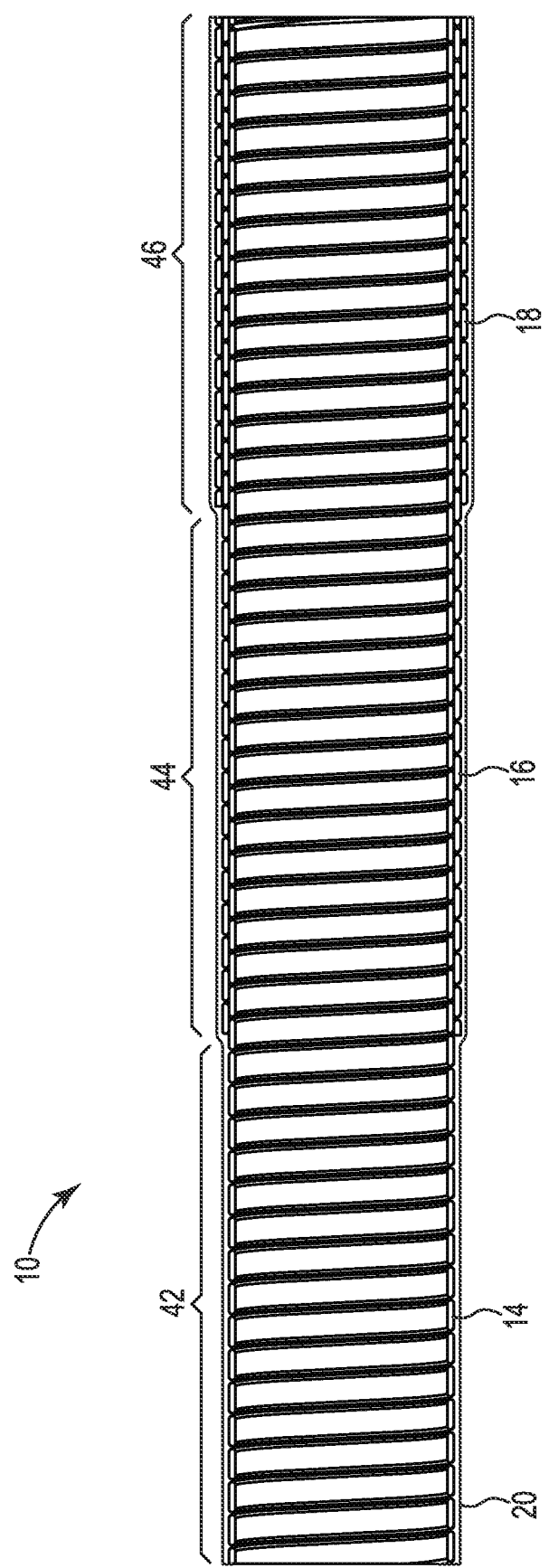

In order to secure partial layers such as illustrated, in some embodiments, some wire layers will be welded to the wire layer below. For example, in FIG. 6a, intermediate wire layer 16 may be welded to inner wire layer 14 at the interface between first and second partial wire layer sections 42 and 44. Similarly, outer wire layer 18 may be welded to intermediate wire layer 16 at the interface between second partial wire layer section 44 and full-wire layer section 46. FIG. 6b further illustrates outer polymer cover 20 over all of the wire layers of torque coil 10. Once fully assembled within outer polymer cover 20, torque coil 10 will have varied flexibility along its length. In first partial wire layer section 42, where only inner wire layer 14 is present, torque coil 10 will have more flexibility than in full-wire layer section 46, where all three layers 14, 16, and 18 are present. The second partial wire layer section 44 will have flexibility between that of first partial wire layer section 42 and full-wire layer section 46.

Figure 6C:
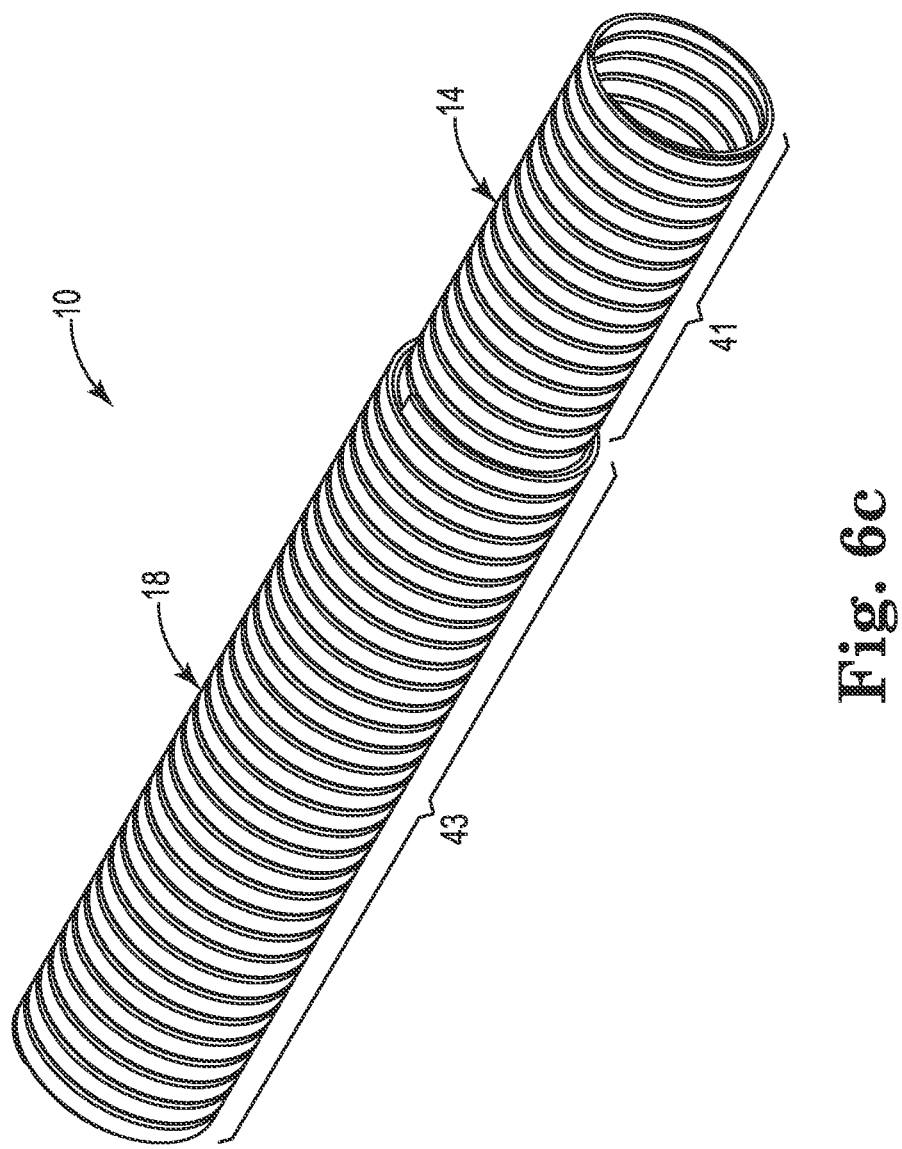

Additional embodiments are possible, for example, FIGS. 6c-6d illustrate inner wire layer 14 is a wire helically wound over a core (not visible in FIGS. 6c-6d) similarly to previously-described embodiments. Intermediate wire layer 16 is then wound over inner wire layer 14, but then terminated such that it covers less than the entire length of torque coil 10. Also in this section, outer wire layer 18 is wound over intermediate wire layer 16. Accordingly, there is a partial wire layer section 41 of torque coil 10 in which only inner wire layer 14 is wound over core 12. Also, there is a full-wire layer section 43 of torque coil 10 in which wire layers 14, 16 and 18 are all present. As in the previous embodiment, in some embodiments, partial wire layers will be welded to the wire layer below. For example, in FIG. 6c, outer wire layer 18 and intermediate wire layer 16 may be welded to inner wire layer 14 at the interface between partial wire layer section 41 and full-wire layer section 43. In the configuration of torque coil 10 illustrated in FIGS. 6c-6d, partial wire layer section 41 has greater flexibility than does full-wire layer section 43, where three wire layers are present.

Such configurations of torque coil 10 in FIGS. 6a-6d are useful in many applications, including vascular applications, where it is helpful to have certain sections of the coil, for example the distal end, more flexible and have certain sections, for example the proximal end, more stiff The configuration of torque coil 10 having sections of different numbers of wire layers as illustrated in FIG. 6a-6d can also be combined with open-wound sections illustrated in FIG. 5 and/or flowing material between adjacent filars illustrated in FIG. 4 in order to create custom flexibility and stiffness.

For example, in full-wire layer section 46 illustrated in FIG. 6b, material 21 from outer polymer cover 20 can be allowed to penetrate between filars 18a of third layer 18, as illustrated in FIG. 4. In this way, full-wire layer section 46 will have even greater relative stiffness than it would have without polymer material penetrating the filars. Also, the filars of wire layers 14, 16, 18 can be open wound within second partial wire layer section 44 of FIG. 6b so that second partial wire layer section 44 will have even greater relative flexibility. Many other combinations of the embodiments illustrated in the figures and herein described are also possible.

Figure 7:
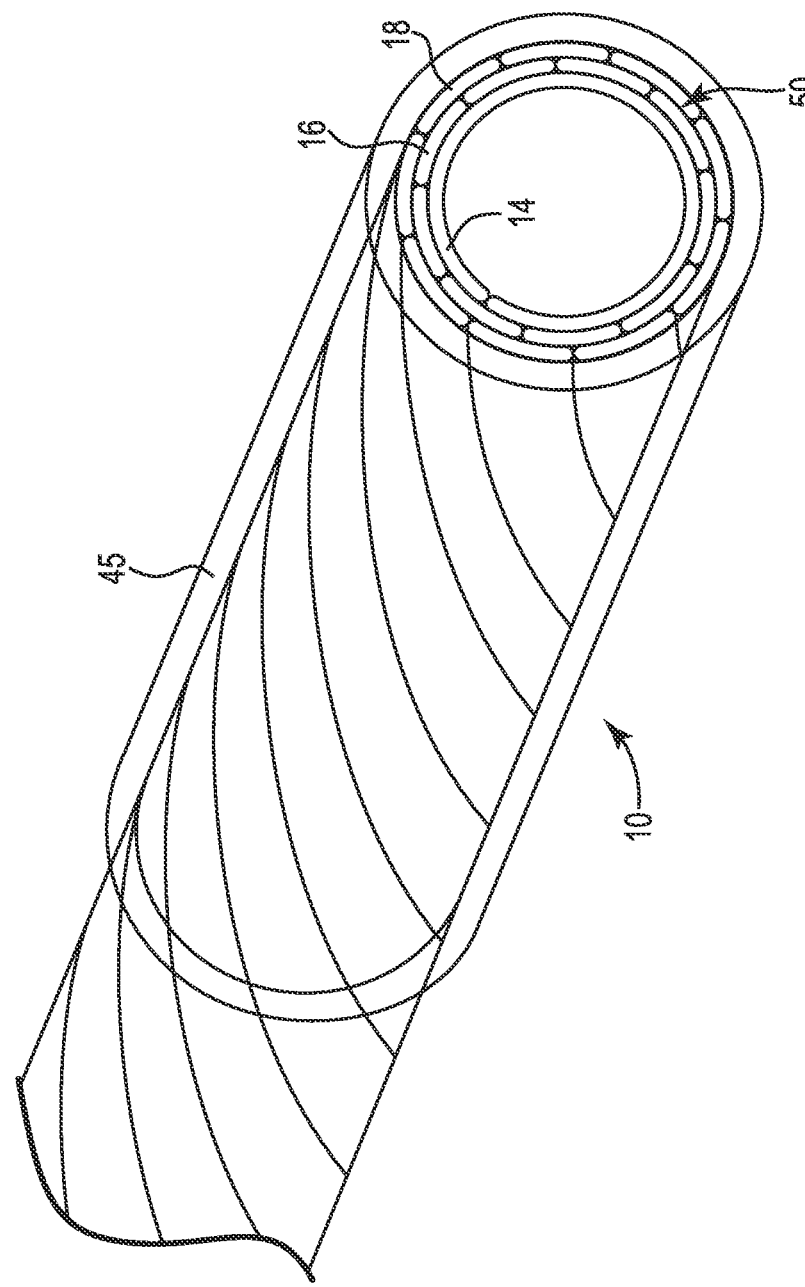
FIG. 7 illustrates an end view of a portion of a torque coil in accordance with one embodiment.

In some embodiments, torque coil 10 can be further secured beyond the securing of layers between core 12 and outer polymer cover 20. FIG. 7 illustrates an end view of a torque coil 10. Wire layers 14, 16 and 18 are helically wound over core 12 (not illustrated in FIG. 7). Clamp 45 (illustrated as ghosted in FIG. 7) is temporally placed over wire layers 14, 16 and 18 to prevent their unwinding. With clamp 45 in place the wire layers 14, 16 and 18 can be welded along their end surface 50. Once wire layers 14, 16 and 18 are secured along the end surface 50 with a weld, clamp 45 can be removed and an outer polymer cover 20 can be added.

In one embodiment, any welding along end surface 50 is limited to only the end surface 50 and is kept to a very limited duration so as to limit any heat damage to core 12. In one embodiment, the welding does not exceed 30 seconds. In other embodiments, end surface 50 is brazed, solder or the like in order to further secure the layers and prevent their unwinding.

In one embodiment, torque coil 10 is assembled one layer at a time. In one embodiment, assembly of torque coil 10 begins with mandrel 11 (illustrate din FIG. 1b. Core 12 is formed over mandrel 11 as a polymer layer using any of a variety of methods of forming polymers over a solid mandrel, such as injection molding, extruding, or the like. Alternatively, torque coil 10 can be formed without mandrel 11, and instead begins with forming core 12 (as in FIG. 1a).

Once core 12 is formed, inner wire layer is wound directly over core 12 in a constrained state. If a single wire is used to form all wire layers within torque coil 10, then the winding of each subsequent layer will constrain each prior layer. For example, winding intermediate wire layer 16 over inner wire layer 14 constrains layer 14. If a wire is cut after winding inner wire layer 14, however, that layer 14 will need to be temporarily constrained until a new wire can be wound over it to form intermediate wire layer 16 over inner wire layer 14 constraining it. In such case, a clamp, such as clamp 45 illustrated in FIG. 7, or similar heat shrink or the like can be used to temporarily constrain inner layer 14 until intermediate wire layer 16 is fully wound over it.

Once intermediate wire layer 16 is fully wound, the process is repeated for any subsequent intermediate layers and for outer wire layer 18. As indicated previously, outer wire layer 18 is constrained by outer polymer cover 20, which can be formed in a variety of ways, including injection molding, extruding or similar methods. Outer wire layer 18 can also be temporarily constrained by clamp, heat shrink or the like until outer polymer cover 20 is fully formed.

In one embodiment, torque coil 10 is configured for very small applications, such as for the vascular system of humans and animals. In some examples, the wire in wire layers 14, 16 and 18 has a wire diameter (WD) as small as 0.0005 inches up to 0.004 inches. In some examples, torque coil 10 has an inner diameter (ID) as small as 0.008 inches up to 0.220 inches, which also defines the diameter of the lumen within inner wire layer 14, and thus the outer diameter of core 12, for torque coil 10. In some examples, the outer diameter (OD) of torque coil 10 is 0.01 inches and 0.250 inches. Different OD and ID sizes for torque coil 10 are also possible where various different size wire is used.

Furthermore, the illustrations herein primarily show the wire that is used in wire layers 14, 16 and 18 as flat or rectangular, but other shapes can be used in accordance with other embodiments. For example, round wire or other shapes can be used. In some embodiments, the wire in wire layers 14, 16 and 18 can be made from one or more of stainless steel, Nitinol®, MP35N, titanium and tantalum. Also, in one embodiment outer polymer cover 20 can be made from one or more of pebax, nylon, PET, FEP, and polyurenthane and core 12 can be made from one or more of polyimide, PTFE, pebax, nylon, polyurethane, HDPE, and PEEK.

Wire layers 14, 16 and 18 can be wound in variety of ways according to embodiments. In one embodiment, one convolution of wire is wound at one time for each of wire layers 14, 16 and 18. In another embodiment, torque coil 10 is a multi-filar coil, where multiple convolutions of adjacent wire are wound at once. Two, three, four, five or more adjacent wire helices can be wound within each layer at one time. Furthermore, each of wire layers 14, 16 and 18 may be wound with a single wire filar, or each layer can be wound with strands of wire so that each layer has adjacent strands of wire.

In embodiments where outer polymer cover 20 is retaining all layers against core 12 and there is no welding or brazing of the wire layers 14, 16, 18, end surfaces, such as end surface 50 in FIG. 7, are relatively clean and smooth areas. As such, other coils, cables and devices can be readily attached. Because torque coil 10 is thus free of any foreign material, such as braze or solder, which can complicate or weaken the attachment of devices, additional devices can readily be attached to torque coil 10 at its ends.

Figure 8:
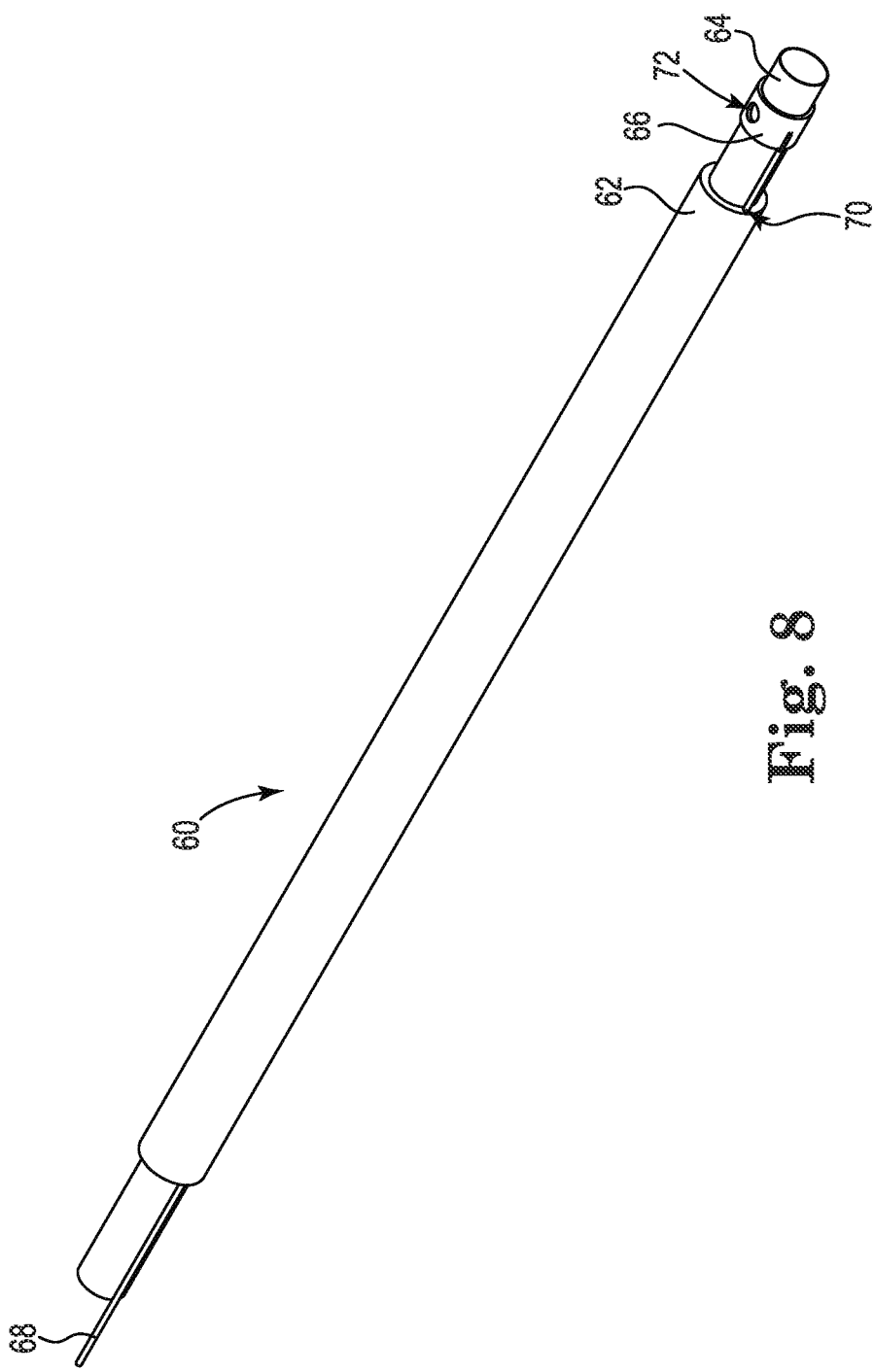
FIG. 8 illustrates a pull-ring catheter in accordance with the prior art.

FIG. 8 illustrates a pull-ring catheter 60 in accordance with the prior art. Pull-ring catheter 60 includes outer jacket 62, inner jacket 64, pull ring 66, pull wire 68 and lumen 70. In some applications, it is useful for a catheter to be deflectable. Deflectable catheters like pull-ring catheter 60 feature a distal tip that can be pulled into a defined curve. This is achieved by using a wire 68 connected to a pull ring 66 near the tip of catheter 60. The distal tip returns to its original shape through natural springback of pull-ring catheter 60.

Although outer jacket 62 is partially cut away in the illustration to show the components below, when fully assembled outer jacket 62 covers pull ring 66 thereby securing ring 66 between outer and inner jackets 62 and 64. Furthermore, pull ring 66 also includes opening 72 such that the material of inner jacket 64 flows through opening 72 further securing ring 66 in place. Wire 68 is fixed to ring 66 via a weld or similar means and then fed back to the proximal end of catheter 60 in lumen 70, which extends through outer jacket 62.

When a user pulls on wire 68 from the proximal end, the distal end of catheter 60 will deflect by virtue of the wire's connection to pull ring 66, which is embedded in outer and inner jackets 62 and 64. Embedding pull ring 66 into jackets 62 and 66, welding wire 66 to pull ring 66, and providing lumen 70 in outer jacket 62, however, all add significant process steps and expense to catheter 60.

Figure 9:
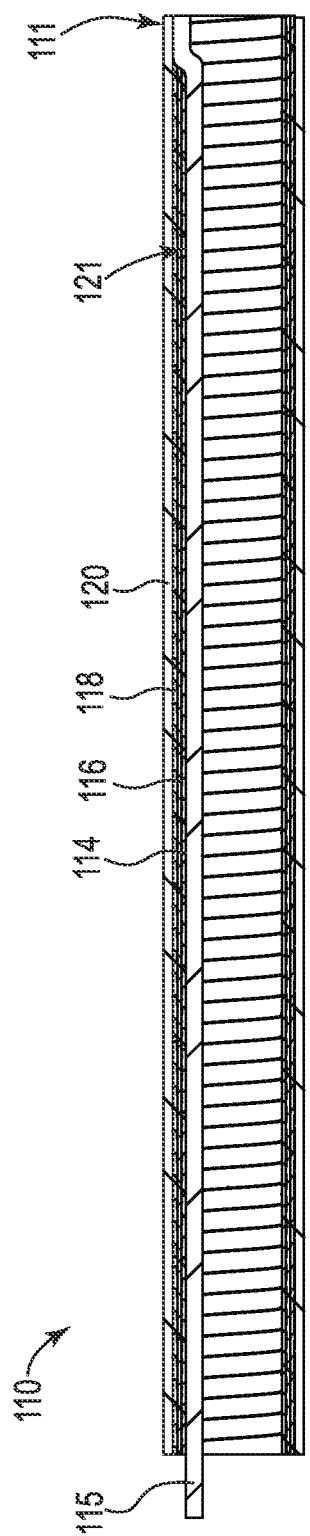
FIG. 9 illustrates a cross-sectional view of a torque coil with pull wire in accordance with one embodiment.

FIG. 9 illustrates torque coil catheter 110 in accordance with one embodiment. Similar to torque coil 10 described above, torque coil catheter 110 can includes a core, but is illustrated without a core for ease of description. Torque coil catheter 110 includes an inner wire layer 114 helically wound over core 12. Additional wire layers 116 and 118 are wound over inner wire layer 114 as described above. Outer polymer cover 120 surrounds wire layers 114, 116 and 118. Torque coil catheter 110 further includes pull wire 115 extending between its proximal and distal ends.

In one embodiment, a small section or groove is made in wire layers 114, 116 and 118 at the distal end of torque coil catheter 110 at connection zone 111. Because wire layers 114, 116 and 118 are typically metal wire, pull wire 115 is readily connectable directly to wire layers 114, 116 and 118 at connection zone 111 via welding or the like. In another embodiment, pull wire 115 can be terminated just short of the distal end, such as two or three inches short of the distal end, and welded, glued or otherwise attached directly to the inner diameter of inner wire layer 114 at alternate connection zone 121.

Once secured directly to one or more of wire layers 114, 116, and 118 at distal end of torque coil catheter 110, pull wire 115 can then be pulled at the proximal end of torque coil catheter 110 to deflect the distal end. Because the entire inner wire layer 114 is typically metal wire, pull wire 115 can be easily connected to any location of the distal end of torque coil catheter 110. Unlike prior systems, no additional pull ring part is necessary allowing both the savings of the cost of the part and its assembly to the catheter.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A torque coil comprising:
an inner wire layer helically wound in a constricted state;
an intermediate wire layer helically wound over the inner wire layer in a constricted state;
an outer wire layer helically wound over the intermediate wire layer in a constricted state;
an outer polymer cover surrounding the inner and outer wire layers thereby securing the wire layers within the outer polymer cover, wherein the outer polymer cover secures the inner, intermediate and outer layers without welding, brazing or soldering;
a penetrated section of the torque coil, including the outer wire and outer polymer cover, where the polymer material of the outer polymer cover penetrates between adjacent filars in the outer wire layer to stiffen the coil in the penetrated section; and
a non-penetrated section of the torque coil, including the outer wire and outer polymer cover, where the polymer material of the outer polymer cover does not penetrate between adjacent filars in the outer wire layer allowing flexibility of the coil in the non-penetrated section;
wherein the torque coil has increased relative flexibility in the non-penetrated section and has decreased relative flexibility in the penetrated section.

2. The torque coil of claim 1 further comprising a core of a polymer material within the inner wire layer, such that the inner and outer wire layers are secured between the core and the outer polymer cover.

3. The torque coil of claim 2, wherein polymer material from the core penetrates between filars in the inner wire layer.

4. The torque coil of claim 1 further comprising:
a tight-wound section wherein at least one of the inner and outer wire layers is tight wound; and
an open-wound section wherein at least one of the inner and outer wire layers is open wound;
wherein the torque coil has increased relative flexibility in the open-wound section and has decreased relative flexibility in the tight-wound section.

5. The torque coil of claim 1 further comprising:
a full-wire layer section wherein both the inner and outer wire layers are within the full-wire layer section; and
a partial-wire layer section wherein the outer wire layer is not within the partial-wire layer section;
wherein the torque coil has increased relative flexibility in the partial-wire layer section and has decreased relative flexibility in the full-wire layer section.

6. The torque coil of claim 1, wherein a pull wire is attached directly to at least one of the wire layers adjacent a distal end of the torque coil.

7. The torque coil of claim 1, wherein the coil is configured for high-speed rotation and one-to-one torque.

8. The torque coil of claim 1, wherein the torque coil comprises an inner lumen having a diameter between 0.008 inches and 0.220 inches, wherein the torque coil has an outer diameter between 0.01 inches and 0.250 inches, and wherein at least one of the inner wire layer and the outer wire layer have a wire diameter between 0.0005 inches and 0.004 inches.

9. A torque coil comprising:
a polymer core;
an inner wire layer helically wound in a constricted state over the polymer core;
an intermediate wire layer helically wound over the inner wire layer in a constricted state;
an outer wire layer helically wound over the intermediate wire layer in a constricted state; and
an outer polymer cover surrounding the inner and outer wire layers thereby securing the wire layers between the polymer core and the outer polymer cover;
a penetrated section of the torque coil, including the outer wire and outer polymer cover, where the polymer material of the outer polymer cover penetrates between adjacent filars in the outer wire layer to stiffen the coil in the penetrated section; and
a non-penetrated section of the torque coil, including the outer wire and outer polymer cover, where the polymer material of the outer polymer cover does not penetrate between adjacent filars in the outer wire layer;
wherein a single filar is used for each of the inner and outer wire layers without being cut; and
wherein the outer polymer cover secures the inner, intermediate and outer layers without welding, brazing or soldering.

10. The torque coil of claim 9, wherein the torque coil has increased relative flexibility in a flexible section and has decreased relative flexibility in a stiff section.

11. The torque coil of claim 10, wherein the stiff section of the torque coil comprises one or more of:
a section wherein the polymer material of the outer polymer cover penetrates between adjacent filars in the outer wire layer in the torque coil;
a section wherein the polymer material of the inner polymer core penetrates between adjacent filars in the inner wire layer;
a section wherein at least one of the inner and outer wire layers is tight wound; and
a section wherein both the inner and the outer wire layer is contained within the stiff section.

12. The torque coil of claim 10, wherein the flexible section of the torque coil comprises one or more of:
a section wherein the polymer material of the outer polymer cover does not penetrate between adjacent filars in the outer wire layer of the torque coil;
a section wherein at least one of the inner and outer wire layers is open wound; and
a section wherein the outer wire layer is not within the flexible section.

13. A method of forming a torque coil comprising:
forming a polymer core;
helically winding an inner wire layer in a constricted state over the polymer core;
helically winding an outer wire layer over the inner wire layer in a constricted state; and
forming an outer polymer cover to surround the inner and outer wire layers thereby securing the wire layers between the polymer core and the outer polymer cover wherein the outer polymer cover secures the inner, intermediate and outer layers without the use of welding, brazing or soldering;
wherein forming the outer polymer cover includes forming a penetrated section of the torque coil such that the polymer material of the outer polymer cover penetrates between adjacent filars in the outer wire layer of the torque coil and includes forming a non-penetrated section of the torque coil such that the polymer material of the outer polymer cover does not penetrate between adjacent filars in the outer wire layer of the torque coil.

14. The method of claim 13 further comprising temporarily securing one of the inner and outer wire layers with a clamp until the outer polymer cover secures the inner and outer wire layers between the core and the outer polymer cover.

15. The method of claim 13, wherein:
forming the outer polymer cover includes controlling the polymer material of the outer polymer cover such that the polymer material penetrates between adjacent filars in the outer wire layer of the torque coil in a penetrated section; and
forming the outer polymer cover includes controlling the polymer material of the outer polymer cover such that the polymer material does not
penetrate between adjacent filars in the outer wire layer of the torque coil in a non-penetrated section such that the torque coil has increased relative flexibility in the non-penetrated section and has decreased relative flexibility in the penetrated section.

16. The method of claim 13, wherein:
winding the inner or outer wire layer includes winding a tight-wound section in which at least one of the inner and outer wire layers is tight wound; and
winding the inner or outer wire layer including winding an open-wound section in which at least one of the inner and outer wire layers is open wound, such that the torque coil has increased relative flexibility in the open-wound section and has decreased relative flexibility in the tight-wound section.

17. The method of claim 13, wherein:

winding the inner and outer wire layer includes winding a full-wire layer section in which both the inner and outer wire layers are within the full-wire layer section; and winding the inner and outer wire layer includes winding a partial-wire layer section in which the outer wire layer is not within the partial-wire layer section, such that the torque coil has increased relative flexibility in the partial-wire layer section and has decreased relative flexibility in the full-wire layer section.

* * * * *